United States Patent [19]
Miller et al.

[11] Patent Number: 5,508,308
[45] Date of Patent: Apr. 16, 1996

[54] USE OF PYRUVYLGLYCINE TO TREAT ISCHEMIA/REPERFUSION INJURY FOLLOWING MYOCARDIAL INFARCTION

[75] Inventors: Robert H. Miller; Mark A. McCamish, both of Worthington, Ohio; Ronald T. Stanko, Pittsburgh, Pa.

[73] Assignee: Abbott Laboratories, Abbott Park, Ill.

[21] Appl. No.: 381,256

[22] Filed: Jan. 31, 1995

Related U.S. Application Data

[60] Continuation-in-part of Ser. No. 43,721, Apr. 8, 1993, which is a division of Ser. No. 868,891, Apr. 16, 1992, Pat. No. 5,256,697.

[51] Int. Cl.$^6$ ................................................. A61K 31/195
[52] U.S. Cl. ............................................................ 514/563
[58] Field of Search ............................................... 514/563

[56] References Cited

U.S. PATENT DOCUMENTS

| | | | |
|---|---|---|---|
| 4,548,937 | 10/1985 | Stanko | 514/251 |
| 5,047,427 | 9/1991 | Williamson | 514/557 |
| 5,210,098 | 5/1993 | Nath | 514/557 |
| 5,256,697 | 10/1993 | Miller et al. | 514/554 |
| 5,283,260 | 2/1994 | Miller et al. | 514/563 |
| 5,294,641 | 3/1994 | Stanko | 514/540 |
| 5,312,985 | 5/1994 | Dhaon et al. | 564/143 |
| 5,395,822 | 3/1995 | Izumi et al. | 514/557 |

FOREIGN PATENT DOCUMENTS

WO9208453  5/1992  WIPO.

OTHER PUBLICATIONS

Salahudeen et al., "Hydrogen Peroxide induced Renal injury" Journal Of Clinical Investigation 88:1886–1893 (1991).

Stanko et al., "Inhibition of Lipid Accumulation and Enhancement of Energy Expenditure by the Addition of Dyruvate and Dihydroxyacetone to a Rat Diet," Metabolism 35(2): 182–186 (1986).

Bünger et al., "Pyruvate enhanced phosphorylation potential and inotropism in normoxic and postischemic isolated working heart," European Journal Of Biochemistry 180:221–233 (1989).

Cavallini et al., "the Protective Action of Pyruvate on Recovery of Ischemic Rat Heart Comparison with Other Oxidizable (1989) Substrates," Journal Of Molecular And Cellular Cardiology 22:143–154 (1990).

Mentzer et al., "Effect of Pyruvate on Regional Ventricular Funtion in Normal & Stunned Myocardium", Annals Of Surgery 209:629–634 (1989).

Mallet et al., "Pyruvate–Enhanced Regional Function and Energetics in Post–Ischemic Canine Myocardium," Federation Of American Societies For Experimental Biology Journal, A326:1890, (1993).

Deboer et al., "Pyruvate enhances recovery of rat hearts after ischemia & reperfusion by preventing free radical generation," American Journal Of Physiology 265:H1571–H1576, (1993).

de Groot et al., "The Effects of exogenous lactate and pyruvate on the recovery of coronary flow in the rat heart after ischaemia," Cardiovascular Research 27:1088–1093, (1993).

Zhou et al., "Effects of Adenosine and Pyruvate on Regional Function and Myocardial Phosphorylation Potential in in vivo Stunned Porcine Myocardium," American Heart Association Abstracts 66th Meeting, I187, No. 0997, (1993).

Ivy et al., "Effect of pyruvate on the metabolism and insulin resistance of obese Zucker rats," American Journal Of Clinical Nutrition 59:331–337, (1994).

Stanko et al., "Body composition, energy utilization, and nitrogen metabolism with a 4.25–MJ/d low–energy diet supplemented with pyruvate," American Journal Of Clinical Nutrition 56:630–635 (1992).

Stanko et al., "Body composition, energy utilization, and nitrogen metabolsim with a severely restricted diet supplemented with dihydroxyacetone and pyruvate," American Journal Of Clinical Nutrition 55:771–776 (1992).

Stanko et al., "Reduction of Carcass Fat in Swine with Dietary Addition of Dihydroxyacetone & Pyruvate," Journal of Animal Science 67:1272–1278 (1989).

Braunwald, Harrison's Principles Of Internal Medicine (13th ed). Ch. 194–195 (1994).

Bonow et al., "Left Ventricular Diastolic Dysfunction as a Cause of Heart Failure," Animals Of Internal Medicine 117:502–510 (1992).

Primary Examiner—José G. Dees
Assistant Examiner—Samuel Barts
Attorney, Agent, or Firm—Donald O. Nickey; Lonnie R. Drayer

[57] ABSTRACT

A therapeutic method is provided to reduce ischemia/reperfusion injury to the heart muscle by perfusing pyruvylglycine into the circulatory system of a patient who has had a heart attack or suffered coronary occlusion.

6 Claims, 2 Drawing Sheets

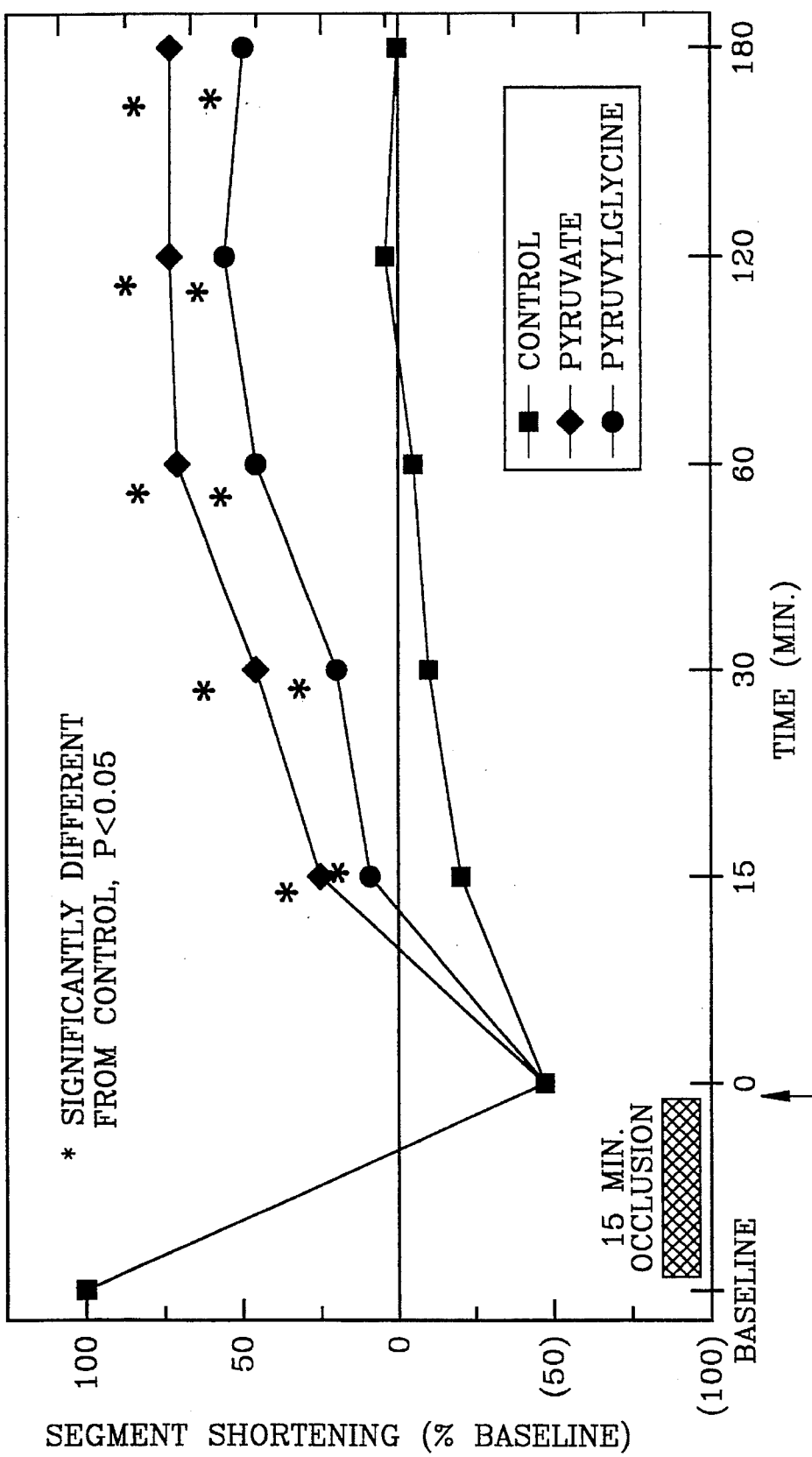

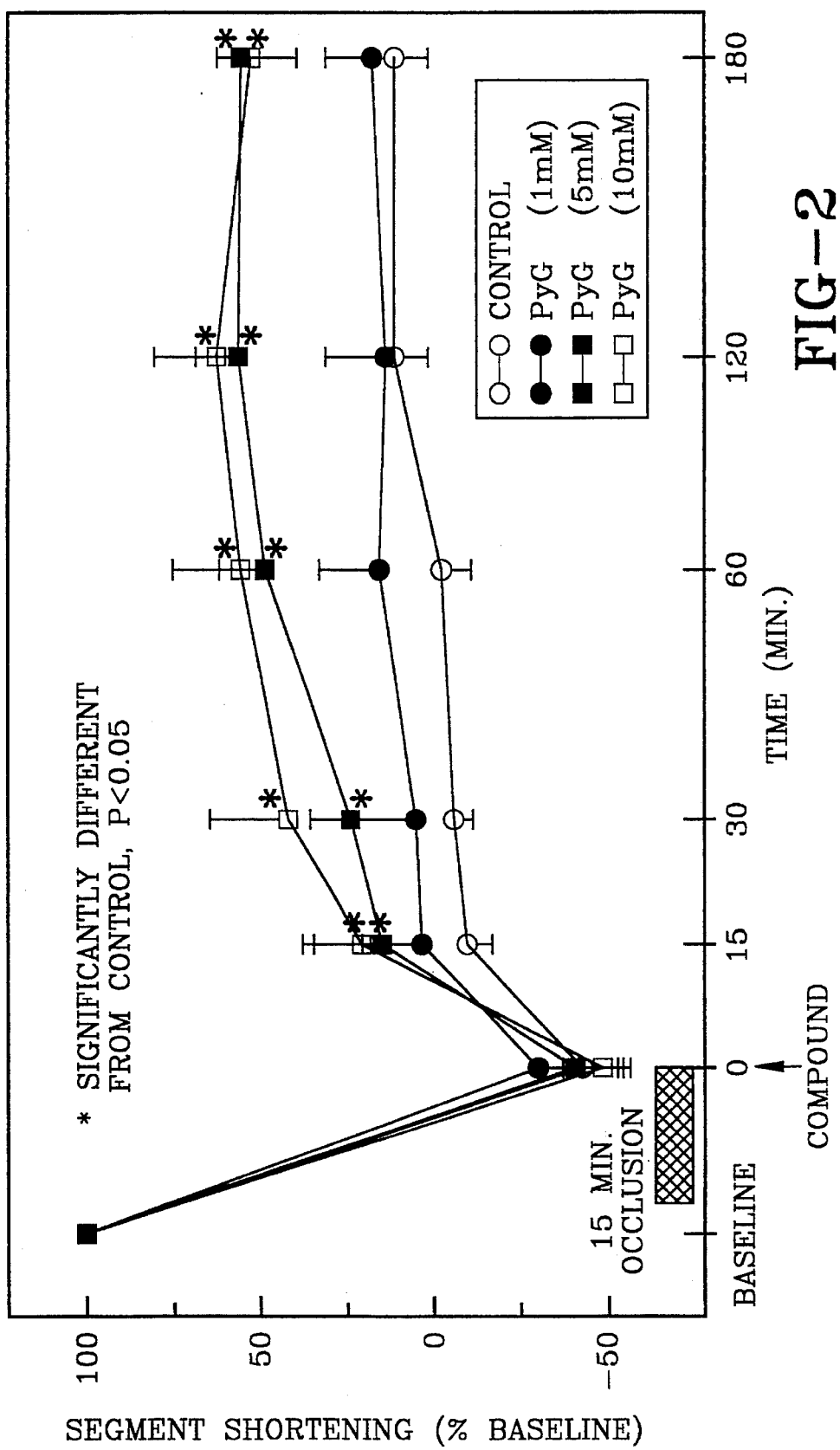

USE OF PYRUVYLGLYCINE TO TREAT ISCHEMIA/REPERFUSION INJURY FOLLOWING MYOCARDIAL INFARCTION

This is a Continuation-in-Part of application Ser. No. 08/043,721 filed Apr. 8, 1993, which is a Divisional of application Ser. No. 07/868,891 filed Apr. 16, 1992 now U.S. Pat. No. 5,256,697 issued Oct. 26, 1993.

TECHNICAL FIELD

The present invention relates generally to a method of administering pyruvylglycine to a patient in order to reduce ischemia/reperfusion damage after treatment for myocardial infarction.

BACKGROUND OF THE INVENTION

Cardiovascular disease is the leading cause of death among Americans. Among those who survive an initial cardiovascular event such as a myocardial infarction or heart attack there is a high level of morbidity resulting from ischemia. As used in the specification and in the claims "ischemia" is defined as a decrease in the blood supply to a bodily organ or tissue caused by constriction or obstruction of the blood vessels. During the acute stage of a heart attack the therapeutic goal is to maintain cardiac function and minimize myocardial muscle damage. This is currently done either by the use of angioplasty or by fibrinolytic treatment of occluded vessels followed by drug therapy. Inotropic agents such as dopamine, dobutamine, isoproterenol, epinephrine and norepinephrine improve ventricular function and maintain cardiac output. These agents, however, increase oxygen requirements and long-term treatment may be harmful to a damaged heart and result in greater cardiac ischemia. Although the initial damage is caused by anoxia, the damage is exacerbated by the sudden reperfusion of oxygen into the heart leading to the generation of free radicals. As used in the specification and in the claims "ischemia/reperfusion injury" refers to the damage to cardiac muscle caused first by restriction of the blood supply followed by a sudden resupply of blood and the attendant generation of free radicals. Other bodily tissues are also subject to reperfusion injury when ischemia, a decrease in the blood supply to the tissue, is followed by reperfusion, a sudden perfusion of oxygen into the deprived tissue. There is a need, therefore, for a treatment for acute cardiac injury that would prevent ischemia and reperfusion injuries, that is damage that results from exposure of the cardiac muscle to reactive oxygen species.

There has been increasing recognition in recent years of the importance of diastolic relaxation during the normal pumping mechanism as well as systolic function, and that diastolic dysfunction can also lead to heart failure (Braunwald, (*Harrison's Principles of Internal Medicine,* 13th ed., Isselbacher, et al.eds.,Ch. 194 and 195, 1994). Bonow et al.,("Left ventricular diastolic dysfunction as a cause of congestive heart failure", Annals of Internal Medicine, 117:502–510, 1992) report that up to 40% of patients presenting with congestive heart failure have preserved left ventricular function and suggest that diastolic dysfunction should be considered in patients with symptoms of heart failure who have normal systolic function. This information suggests that an agent that improved diastolic dysfunction, i.e., a lucinotropic agent, would be beneficial, as well as an agent that improved systolic function, i.e., an inotropic agent, in treating chronic or acute cardiac failure.

Pyruvate is a metabolically active compound common to metabolic pathways of glucose, lipid, and amino acids in animals.

In the heart it serves as an energy-yielding substrate. In preclinical studies it has been shown to increase metabolic rate, reduce weight and fat gain and improve insulin sensitivity in diabetic animals. It has also been demonstrated to be an effective antioxidant that reduces damage to heart tissue during ischemia and reperfusion injury.

Pyruvate is active when administered both enterally and parenterally. However, when administered enterally it must be in the form of a mineral salt. This has the negative side-effect of delivering excessive amounts of electrolytes such as sodium ($Na^+$), calcium ($Ca^{2+}$), or potassium ($K^+$). The propyruvate, pyruvylglycine, was developed to avoid the excessive intake of pyruvate salts, which would result in, for example, sodium overload in cardiac patients.

Neither pyruvate nor pyruvylglycine is known to be acutely toxic. Both have been fed at high levels, 10% of the diet, for up to 28 days to laboratory animals with no noticeable toxic effects seen either on necropsy or pathological review.

Pyruvate has been tested for activity in treating obesity, diabetes and damage to kidney cells. Salahudeen et al. ("Hydrogen Peroxide-induced Renal Injury", *Journal of Clinical Investigation,* 88:1886–1893, 1991) found that pyruvate protects renal tissue in vitro and in vivo from injury caused by the strong oxidant, hydrogen peroxide ($H_2O_2$). When the diet of pigs (Stanko et al , "Reduction of Carcass Fat in Swine With Dietary Addition of Dihydroxyacetone and Pyruvate", *Journal of Animal Science,* 67:1271–1278, 1989) or rats (Stanko et al., "Inhibition of Lipid Accumulation and Enhancement of Energy Expenditure by the Addition of Pyruvate and Dihydroxyacetone to a Rat Diet", *Metabolism,* 35:2,182–186,1986) was supplemented with pyruvate the rates of weight gain and fat deposition were reduced. Pyruvate supplementation of weight reduction diets for obese human subjects also resulted in increased weight and fat loss when compared to controls (Stanko et al., "Body composition, energy utilization, and nitrogen metabolism with a 4,25-Mj/d low-energy diet supplemented with pyruvate", *American Journal of Clinical Nutrition,* 56:630–635, 1992; Stanko et al., "Body composition, energy utilization, and nitrogen metabolism with a severely restricted diet supplemented with dihydroxyacetone and pyruvate", *American Journal of Clinical Nutrition,* 55:771–776, 1992). U.S. Pat. No. 5,047,4270 (Williamson, "Treatment for Secondary Diabetes Effects" discloses that pyruvate is effective in preventing vascular damage in diabetic rats.

Several patents teach the use of pyruvate in the management of obesity problems and improving insulin resistance and disclose methods of synthesizing modifications of pyruvate (pyruvate analogs), which may eliminate the problem of electrolyte overload which occurs when pyruvate is administered in the form of a pyruvate salt.

U.S. Pat. No. 4,548,937 (Stanko et al., "Method for Preventing Body Fat Deposition in Mammals") discloses a method for minimizing weight gain by adding pyruvate to the diet. U.S. Pat. No. 5,256,697 (Miller et al., "Method of Administering Pyruvate and Methods of Synthesizing Pyruvate Precursors") discloses a method of minimizing weight gain by administering pyruvate precursors orally in the diet. Pyruvate precursors, also known as pyruvate analogs, were synthesized in order to avoid the well-known problems ensuing from ingesting large amounts of salts which previously accompanied the ingestion of pyruvate. U.S. Pat. No.

5,312,985 (Dhaon et al., "Method of Synthesizing the Pyruvate Precursor Pyruvamide") was filed as a divisional of U.S. Pat. No. 5,256,697. Dhaon et al. claim a novel method of synthesizing a pyruvate analog, pyruvamide, which can be tested for efficacy in the management of various human metabolic diseases. Dhaon et al. also disclose a novel method of synthesis of various pyruvate analogs, particularly pyruvyl-amino acids, in which covalently linked amino acids replace the salts complexed to pyruvate. Pyruvylglycine was among the pyruvate analogs synthesized.

U.S. Pat. No. 5,283,260 (Miller et al., "Method for Reducing Insulin Resistance in Mammals") was also filed as a divisional of what is now U.S. Pat. No. 5,256,697. In U.S. Pat. No. 5,283,260 Miller et al. claim a method of reducing insulin resistance by orally administering a pyruvyl-amino acid. Pyruvylglycine was shown to be effective in reducing insulin resistance when added to the diet of obese and diabetes-prone rats and, thus, useful in the management of Type II diabetes.

The two patents to Miller et al. and the patent to Dhaon et al. disclose the efficacy of pyruvate analogs, particularly pyruvylglycine, in the management of obesity related problems and excessive food intake. They also disclose a superior synthesis of some pyruvate analogs. However, they do not disclose the use of pyruvylglycine in treating heart disease, and, as will be shown below, the efficacy of pyruvylglycine in any particular application is presently neither predictable nor obvious. It is only possible to determine experimentally whether a particular pyruvate analog will be safe and efficacious in the management of a given medical condition.

There is also a substantial body of basic research into the effect of pyruvate on heart . Bunger et al. ("Pyruvate-enhanced phosphorylation potential and inotropism in normoxic and postischemic isolated working heart" *European Journal of Biochemistry*, 180:221–233, 1989) demonstrated the cardioprotective effect of pyruvate on guinea pig hearts during hypoxia, ischemia and reperfusion. Cavallini et al., ("The Protective Action of Pyruvate on Recovery of Ischemic Rat Heart: Comparison with Other Oxidizable Substrates" *Journal of Molecular and Cellular Cardiology*, 22:143–154, 1990) reported the protective action of pyruvate on ischemic rat hearts. The data of Mentzer et al. ("Effect of Pyruvate on Regional Ventricular Function in Normal and Stunned Myocardium", *Annals of Surgery*, 209:629–634, 1989) indicate that pyruvate enhances ventricular function in post-ischemic dog hearts. Pyruvate improved cardiac function in reperfused post-ischemic canine hearts (Mallet et al., "Pyruvate Enhanced Regional Function and Energetics in Post-Ischemic Canine Myocardium", *Federation of American Societies for Experimental Biology Journal*, A326:No.1890, 1993) and in rat hearts (DeBoer et al, "Pyruvate enhances recovery of rat hearts after ischemia and reperfusion by preventing free radical generation", *American Journal of Physiology*, 265:H1571-H 1576, 1993) and de Groot et al., "The effects of exogenous lactate and pyruvate on the recovery of coronary flow in the rat heart after ischaemia", *Cardiovascular Research*, 27:1088–1093,1993) Zhou et al. reported at the 66*th Meeting* of the *American Heart Association*, ("Effects of Adenosine and Pyruvate on Regional Function and Myocardial Phosphorylation Potential in in vivo Stunned Porcine Myocardium", I-187 No 0997 1993) that treatment with pyruvate, 60 minutes after arterial occlusion of porcine hearts, during the last 30 minutes of reperfusion attenuated myocardial stunning.

U.S. Pat. No. 5,294,641 (Stanko, "Method for Treating a Medical Patient for Cardiac Trauma") teaches the use of pyruvate in the treatment of myocardial infarction and ischemia in order to reduce the oxygen demand of the heart.

Due to the importance of the problem of reperfusion injury, many compounds have been tested for efficacy. WO 92/08453 (Davies et al., "Hydroxamic Acids for Preventing Reperfusion Injury") discloses that various hydroxamic acid derivatives act as antioxidants in an in vitro system. Davies et al. teach the use of hydroxamic acids in the prevention and treatment of reperfusion injury.

The preceding references demonstrate that pyruvate is a cardioprotective substrate after hypoxic or ischemic damage to the heart such as occurs during coronary surgery. However, in order to administer effective doses of pyruvate under clinical conditions the required blood concentration of pyruvate would result in the patient receiving excessively high levels of electrolytes. There is, therefore, a need for an improved method of delivering pyruvate to patients with cardiovascular disease which would not require harmful levels of mineral salts and would confer the cardioprotective benefits of pyruvate.

SUMMARY OF THE INVENTION

The present invention provides a therapeutic method comprising administration of pyruvylglycine, an analog of pyruvate, to patients who have had heart attacks to prevent ischemic/reperfusion injuries both during the coronary artery event and during subsequent medical procedures. There is disclosed a method of administering pyruvate to mammals, which comprises administering a therapeutically effective amount of the pyruvate precursor, pyruvylglycine, to prevent secondary myocardial damage.

BRIEF DESCRIPTION OF THE DRAWINGS

FIG. 1 shows the effect of pyruvate and pyruvylglycine compared with saline controls on segment shortening in the stunned myocardium of dogs.

FIG. 2 shows the effect of different concentrations of pyruvylglycine on regional myocardial segment shortening in the ischemic/reperfused region of the stunned myocardium of dogs.

DETAILED DESCRIPTION OF THE INVENTION

There is substantial evidence that pyruvate provides protection to mammalian heart muscle which has been deprived of a blood supply and, therefore, of oxygen. This can occur during a heart attack or can be simulated experimentally in animals. Because of the further deleterious effect on the myocardium of subsequent necessary medical interventions and because of the burden to the recipient of excessive amounts of electrolytes when pyruvate is administered in the form of pyruvate salts, a method of administering pyruvate in the form of a pyruvyl amino acid, pyruvylglycine, is disclosed.

Although pyruvate appears to be an efficacious compound in the treatment of obesity, Type II or Non-insulin Dependent Diabetes mellitus (NIDDM), acute renal failure, and cardiac ischemic/reperfusion injury, the clinical utility of pyruvate has been limited by the elevated mineral load associated with pyruvate salts. A discovery process was, therefore, undertaken to find alternative forms of pyruvate which would combine both efficacy and greater safety.

The most preferred method of synthesizing pyruvylglycine was disclosed in U.S. Pat. No. 5,256,697 (Miller et al., "Method of Administering Pyruvate and Methods of Synthesizing Pyruvate Precursors") at columns 7 and 8. This is a one-step synthesis that has a productivity level similar to or superior to traditional methods of synthesizing pyruvylglycine. The synthesis of pyruvylglycine comprises charging a 2 L flask (air stirrer, condenser, nitrogen inlet) with glycine (15 g, 0.2 mol), anhydrous acetonitrile (ACN) and trimethylsilyl chloride ((30.5 Ml, 0.24 mol). The reactants are stirred at reflux for 3 hours. The clear turbid solution is then cooled to 5° C. in an ice bath and propylene oxide (100 Ml) is added at once. In a separate flask, oxalyl chloride (21 mL, 0.24 mol) is added to sodium pyruvate (24.2 g, 0.22 mol) in ACN (500 mL) at 0° C. with vigorous degassing. The solution is stirred at 25° C. for 3 hours under a blanket of nitrogen. The slurry is cooled to 5° C. and added in one portion to the above trimethylsilyl ester solution at 5° C. The sodium chloride is not filtered off at this stage. The slurry is stirred at 5° C. for about 2 hours and then warmed to 25° C. and held overnight. Methanol (80 mL) is added at once, the salts are filtered off and the solvents are evaporated at a temperature of less than 35° C. The residue (about 74 g) is flash-filtered through a bed of silica (200 g) with ethyl acetate/heptate (1:1). The fractions containing the product are concentrated to a solid mass (26 g, 90%). Following recrystallization from chloroform/heptane (1:3 1500 mL) a tan solid is obtained, melting point 87° C. (21.9 g, 75%). The pyruvylglycine is recrystallized using any suitable procedure such as freeze drying, spray drying or microwave vacuum drying.

The following examples show that pyruvylglycine does not operate through the same mechanism as pyruvate and that it has different and presently unpredictable effects in different organ systems. Pyruvylglycine should not only be of value in the treatment of patients who have experienced a myocardial infarction in order to control reperfusion injury on the sudden resupply of oxygen to heart tissue, but also in the control of reperfusion damage upon the resupply of oxygen to other tissues which have suffered ischemia and hypoxia. The examples are meant for illustrative purposes only and should not be construed as limiting the claims of the invention.

EXAMPLE 1-COMPARATIVE STUDIES

Two studies were designed to compare the efficacy of pyruvate and pyruvylglycine in protecting renal cells from damage by the strong oxidant $HaO_2O_2$. It is known that administration of a pyruvate salt is an effective method of treating renal failure (U.S. Pat. No. 5,210,098, Nath, "Use of Pyruvate to Treat Acute Renal Failure"). Salahudeen et al., ("Hydrogen Peroxide-induced Renal Injury", *Journal of Clinical Investigation*, 88:1886–1893, 1991) showed that administration of sodium pyruvate in vitro and in vivo protects renal tissue from $H_2O_2$ mediated damage.

Renal tubular epithelial cells (LLC-$PK_1$) were grown in Dulbecco's modified Eagle's medium (DME), transferred in DME to 24-well plates and studied as a confluent layer. LLC-$PK_1$ cells were radiolabeled by incubating each well with 2.0 μCi [$^{51}Cr$]chromate. Cells were washed and placed in pyruvate-free basal medium Eagle's (BME) with 100 mg/dl glucose. The monolayers were treated with $H_2O_2$, either 2 mM of sodium pyruvate or 2 mM of pyruvylglycine was added, and the cells were incubated for six hours. BME was then aspirated from each well, the cells were washed and centrifuged. Cytotoxicity induced by $H_2O_2$ was measured by determining the amount of $^{51}Cr$ released. Cytolytic release of $^{51}Cr$, $^{51}Cr$ in cells that had detached from the monolayer, and $^{51}Cr$ in remaining adherent cells, which represent remaining viable cells, were counted separately. Cell damage was quantified by measuring extracellular release of $^{51}Cr$ caused by cell lysis and detachment.

Table I compares extracellular chromium release in cells exposed to $H_2O_2$ which were not treated with an antioxidant, cells treated with pyruvate, and cells treated with pyruvylglycine. Pyruvate, but not pyruvylglycine, protected the cells from hydrogen peroxide damage.

The LLC-PK cell system was also used to compare the ability of pyruvate and pyruvylglycine to protect cultured renal cells against intracellular oxidant damage by $H_2O_2$. Intracellular damage from exposure to $H_2O_2$ was induced by adding to the cell culture 250 μM of CDNB, an electrophilic agent, and 10 Mm of aminotriazole (AT), a catalase inhibitor. The application of these compounds resulted in significant cytolysis. Table II indicates the level of protection against intracellular injury by $H_2O_2$ by pyruvate and pyruvylglycine when compared with a control. Again, pyruvate was most effective in protecting cells against damage by an oxidant. In this case, however, pyruvylglycine did provide some protection as evidenced by a 35% reduction in $^{51}Cr$ release. As expected, however, sodium pyruvate was a better hydrogen peroxide scavenger than pyruvylglycine, and, therefore, afforded better protection than pyruvylglycine.

The results shown in Tables I and II of the studies of the inhibition of both extracellular and intracellular damage to renal cells are illustrative of the fact that pyruvate and pyruvylglycine do not operate by identical mechanisms and that the effectiveness of pyruvylglycine in a particular organ system cannot be anticipated by extrapolating from the known effect of pyruvate, but must be determined experimentally.

TABLE I

INHIBITION OF EXTRACELLULAR OXIDANT DAMAGE IN RENAL TUBULAR EPITHELIAL CELLS

| Treatment | Chromium Release (%/hr)[1] |
| --- | --- |
| $H_2O_2$ only (Control) | 31.72 ± 5.54 |
| 2 mM Pyruvate | 5.76 ± 1.90 |
| 2 mM Pyruvylglycine | 34.02 ± 4.98 |

[1]Mean ± SEM, n = 10

TABLE II

INHIBITION OF INTRACELLULAR OXIDANT DAMAGE IN RENAL TUBULAR EPITHELIAL CELLS

| Treatment | Chromium Release (%/hr)[1] |
| --- | --- |
| $H_2O$ + CDNB + AT (Control) | 40.66 ± 4.8 |
| 2 mM Pyruvate | 6.72 ± 2.13 |
| 2 mM pyruvylglycine | 26.20 ± 6.07 |

[1]Mean ± SEM, n = 5

EXAMPLE 2—COMPARATIVE STUDY

The following study was designed to investigate the effect of pyruvate and pyruvylglycine on obese rats susceptible to Type II (NIDDM) diabetes. Obese female Zucker rats were used as a model of obesity related Type II diabetes. The effect of pyruvate and of pyruvylglycine on resting energy expenditure (REE), respiratory quotient (RQ), insulin levels, and insulin-glucose index (the product of glucose and insulin areas in an oral glucose tolerance test) were compared. Five week old obese female Zucker rats were randomly assigned to a control diet or one of two experimental diets. The experimental diets contained by weight either 6% pyruvylglycine or pyruvate and the rats were pair-fed for three weeks. Results as reported by Ivy et al., "Effects of pyruvate on the and insulin resistance of obese Zucker rats", *American Journal of Clinical Nutrition,* 59:331–337, (1994) are shown in Table III. The results indicate that pyruvate and pyruvylglycine affect REE and RQ similarly, but that pyruvylglycine is more effective than pyruvate in improving insulin sensitivity.

The data show that while the effect of pyruvate and pyruvylglycine on REE and RQ is similar, pyruvylglycine is somewhat more effective in improving sensitivity to insulin. This illustrates once again that the modes of action of pyruvate and pyruvylglycine are not identical and that it is not possible to predict with accuracy the effect of pyruvylglycine from what is known about pyruvate.

TABLE III

EFFECT OF PYRUVATE AND PYRUVYLGLYCINE IN THE OBESE ZUCKER RAT[1]

| Treatment | REE $VO_2$,mL/min/kg | RQ $CO_2/O_2$ | Insulin nmol/L | Insulin-Glucose Index $\times 10^{-3}$ |
|---|---|---|---|---|
| Control | 7.05 ± 0.44 | 0.859 ± .025 | 1.89 ± 0.15 | 94.2 ± 10.9 |
| Pyruvate | 8.00 ± 0.25 | 0.771 ± .009[2] | 1.40 ± 0.09[2] | 83.3 ± 9.4 |
| Pyruvylglycine | 8.20 ± 0.19[2] | 0.777 ± .009[2] | 1.12 ± 0.13[2] | 59.6 ± 4.4[2] |

[1]Mean ± SEM
[2]Significantly different from control group at $p < 0.05$

EXAMPLE 3—COMPARATIVE STUDY

The results of much basic research substantiate the beneficial effect of pyruvate in protecting the heart from damage due to ischemia/reperfusion. The cardioprotective effect of pyruvate has been demonstrated with guinea pigs, rats, dogs and pigs. Use of pyruvate in its usual form, as a pyruvate salt, presents a clinical problem, however, because of its high salt content. Pyruvylglycine, a pyruvate analog, was, therefore, tested as an alternative therapy which would eliminate the problem of electrolyte overload.

A study was undertaken to assess the cardioprotective effects of pyruvate and pyruvylglycine following ischemia/reperfusion injury in dogs. The results are shown in Table IV. Eight dogs were assigned to each of three groups. The dogs were well-matched before and during the study as evidenced by heart rate, mean arterial pressure, rate-pressure product, left ventricle pressure change and coronary blood flow. As indicated in Table IV, pyruvate, but not pyruvylglycine, was found to act as a mild vasodilator as seen by a slight increase after occlusion of coronary blood flow (CBF). There were no differences in blood gases and pH between the groups.

TABLE IV

CORONARY BLOOD FLOW (ml/min)[1]

| | Baseline | Rep:30 min | Rep:1 hr | Rep:2 hrs | Rep:3 hrs |
|---|---|---|---|---|---|
| Control | 36 ± 4 | 44 ± 7 | 46 ± 8 | 43 ± 8 | 39 ± 6 |
| Pyruvate | 33 ± 4 | 54 ± 7 | 51 ± 6 | 49 ± 6 | 48 ± 6 |
| Pyruvylglycine | 31 ± 5 | 30 ± 2 | 29 ± 2 | 32 ± 3 | 30 ± 3 |

[1]Values given as mean ± S.E.M.

One group of dogs was assigned to receive saline during reperfusion; the other two received either pyruvate or pyruvylglycine. The dogs were anesthetized and ischemia was induced by occluding the left anterior descending (LAD) coronary artery for 15 minutes followed by reperfusion for 3 hour with saline, pyruvate, or pyruvylglycine. When blood flow was resumed, saline, 10 mM pyruvate, or 5 mM pyruvylglycine was perfused directly through the coronary artery into the ischemic area. This was continued throughout the 3 hour period of reperfusion.

The prolonged ventricular dysfunction that occurs after brief periods of coronary artery occlusion that does not result in irreversible damage to the myocardium is termed the "stunned myocardium". The aim of this study was to determine the effect of pyruvate and pyruvylglycine on the recovery of regional segment function in the stunned myocardium of anesthetized dogs. Myocardial function was assessed by measuring segmental shortening ($\Delta$SS,dP/dt) in the stunned myocardium upon reperfusion. The ischemic area in all groups was approximately 30% of the left ventricle. This similarity in the size of the ischemic area indicates that all groups were subjected to substantially equivalent degrees of ischemia during the 15 minute occlusion period.

The greatest difference between groups was seen in the change in segment shortening in the ischemic area upon reperfusion. Segment shortening is a measure of the length of the muscle segment during diastole and systole divided by the normal segment shortening. As seen in FIG. 1, all groups showed profound inhibition of normal segment shortening during ischemia. Upon reperfusion the control group returned to 2% of normal, i.e. baseline; the pyruvate group returned to 70% of normal; and the pyruvylglycine group returned to 52% of normal. These results are represented graphically in FIG. 1, which shows the effect of pyruvate and pyruvylglycine compared with saline controls on segment shortening in stunned myocardium of dogs.

The results of the study are in agreement with prior observations of the ability of pyruvate to attenuate reperfusion injury (Mallet et al., "Pyruvate-Enhanced Regional Function and Energetics in Post-Ischemic Canine Myocardium", *Federation of American Societies of Experimental Biology Journal,* A326:Abstract 1890, 1993). Pyruvylglycine is also shown to improve functionality of the stunned myocardium although the magnitude of the improvement was less, but not significantly less, than for pyruvate. It is possible that the somewhat lesser improvement seen with pyruvylglycine may be due to the lower concentration used. The mechanism by which improved functionality is accomplished is not well understood and may include an inotropic, i.e. systolic, or a lucinotropic, i.e. diastolic effect.

EXAMPLE 4—COMPARATIVE STUDY

Another study was undertaken to determine the effect of different doses of pyruvylglycine on the recovery of regional segment function in stunned myocardium. The doses tested were 1, 5, and 10 mM pyruvylglycine. Anesthetized dogs were subjected to 15 minutes of coronary artery occlusion followed by three hours of reperfusion. One of the three concentrations of pyruvylglycine was administered through the coronary artery into the ischemic/reperfused area beginning at the onset of reperfusion and continuing through the remainder of the reperfusion period. While in the studies reported here pyruvylglycine was administered into a coronary artery, it is within the scope of the present invention to treat ischemia/reperfusion injury by administering the pyruvate into any suitable artery.

The effects of the three different doses of pyruvylglycine on regional segment shortening in the ischemic/reperfused area can be seen in FIG. 2. Pyruvylglycine resulted in a dose-dependent improvement in regional segment shortening in the ischemic area at all times measured throughout reperfusion as compared to the control group. The least improvement resulted from treatment with 1 mM pyruvylglycine. A greater and statistically significant improvement, when compared to the control, was seen with the administration of either 5 or 10 mM. There was no statistically significant difference between the groups treated with either 5 or 10 mM. The results of this study indicate that administering pyruvylglycine at a concentration between 1 mM and 10 mM into an artery of a person who has had a heart attack or suffered coronary occlusion is an effective method of treating ischemia/reperfusion injury.

The mechanism of action of pyruvate and pyruvylglycine are not well understood in different disease states. What is clear, however, is that pyruvate supplementation results in altered metabolic and/or physiologic responses in several different situations and that the action of pyruvylglycine cannot be predicted with certainty from results obtained with pyruvate. Three possible pathways have been suggested for the action of pyruvate resulting in observed physiological effects. Pyruvate may act as: (1) an antioxidant; (2) a modulator of redox state through lactate and pyruvate dehydrogenases; and (3) an energy substrate for the cell during Krebs Cycle. It is not presently known whether pyruvylglycine acts similarly in any of these pathways or whether it operates through another mechanism, such as an inotropic or lucinotropic effect.

What is claimed is:

1. A method for treating ischemia/reperfusion injury of the coronary muscle, which method comprises administering a therapeutically effective amount of pyruvylglycine into the circulatory system.

2. A method for treating ischemia/reperfusion injury according to claim 1, wherein pyruvylglycine is administered into a coronary artery.

3. A method for treating ischemia/reperfusion injury according to claim 1 wherein the pyruvylglycine is administered at a concentration between 1 and 10 mM.

4. A method for enhancing recovery of regional segment function in a stunned myocardium of a mammal following myocardial injury by parenterally administering a therapeutically effective amount of pyruvylglycine into the circulatory system.

5. A method for enhancing recovery of regional segment function in a stunned myocardium according to claim 4, wherein the pyruvylglycine is administered into a coronary artery.

6. A method for enhancing performance of regional segment function in an injured myocardium of a mammal by administering a therapeutically effective amount of pyruvylglycine.

* * * * *